United States Patent [19]

Shutske et al.

[11] Patent Number: 5,401,749

[45] Date of Patent: * Mar. 28, 1995

[54] 9-AMINO-1,4ETHANO-1,2,3,4-TETRAHYDROACRIDINE AND RELATED COMPOUNDS

[75] Inventors: Gregory M. Shutske, Somerset; Kevin J. Kapples, Little York, both of N.J.

[73] Assignee: Hoechst-Roussel Pharmaceuticals Inc., Somerville, N.J.

[*] Notice: The portion of the term of this patent subsequent to Jan. 30, 2007 has been disclaimed.

[21] Appl. No.: 218,755

[22] Filed: Jul. 8, 1988

Related U.S. Application Data

[63] Continuation-in-part of Ser. No. 14,753, Feb. 13, 1987, Pat. No. 4,897,400.

[51] Int. Cl.$^6$ .................. C07D 221/18; A61K 31/435
[52] U.S. Cl. .......................... 514/289; 546/74
[58] Field of Search ........................... 546/74; 514/289

[56] References Cited

U.S. PATENT DOCUMENTS

| | | | |
|---|---|---|---|
| 3,232,945 | 2/1966 | Sigal, Jr. et al. | 546/93 |
| 3,318,895 | 5/1967 | Pribyl et al. | 546/93 |
| 3,318,896 | 5/1967 | Pribyl et al. | 546/93 X |
| 3,541,066 | 11/1970 | Wolf | 546/63 |
| 3,580,915 | 5/1971 | Wolf et al. | 546/63 |
| 3,637,706 | 1/1972 | Wolf et al. | 544/361 |
| 3,647,800 | 3/1972 | Wolf et al. | 546/81 |
| 3,657,233 | 4/1972 | Wolf et al. | 544/127 |
| 3,674,790 | 7/1972 | Wolf et al. | 546/81 |

(List continued on next page.)

FOREIGN PATENT DOCUMENTS

| | | |
|---|---|---|
| 0179383 | 4/1986 | European Pat. Off. . |
| 0268871 | 6/1988 | European Pat. Off. . |
| 1022940 | 3/1966 | United Kingdom ................. 546/79 |

OTHER PUBLICATIONS

Abramochkin, et al., Khim.-Farm. Zh., English language version vol. 4(7), pp. 10–13 (1970).

Konshin, et al.(I), Khim.-Farm. Zh., English language version vol. 5(11), pp. 10–12 (1971).

Konshin, et al.,(II), Izv.Vyssh,Ucheb.Zaced.Khim.-Khim Tekhnol., vol. 15(2), pp. 243–244 (1972) English language version.

(List continued on next page.)

Primary Examiner—John M. Ford
Attorney, Agent, or Firm—Barbara V. Maurer; Tatsuya Ikeda

[57] ABSTRACT

There are disclosed compounds having the formula

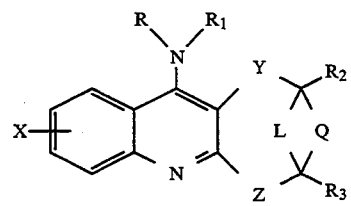

wherein R is hydrogen, loweralkyl or loweralkylcarbonyl; $R_1$ is hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; $R_2$ and $R_3$ are independently H or $CH_3$; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_4$ or —NR$_5$R$_6$ where $R_4$ is hydrogen or loweralkyl, and $R_5$ and $R_6$ are independently hydrogen, loweralkyl or cycloalkyl; Y and Z are independently a direct bond, $CR_7 R_8$ or $CR_7R_8$—$CR_9R_{10}$; and L and Q are independently $CR'_7R'_8$, $CR'_7R'_8$—$CR'_9R'_{10}$, $CR'_7$=$CR'_9$ or $CR'_7R'_8$—$CR'_9R'_{10}$—$CR_{11}R_{12}$, where each of $R_7$ through $R_{12}$ and $R'_7$ through $R'_{10}$ is independently H or $CH_3$; a stereo, optical and geometrical isomers thereof, and pharmaceutically acceptable acid addition salts thereof, which are useful for enhancing memory.

12 Claims, No Drawings

U.S. PATENT DOCUMENTS

| | | | |
|---|---|---|---|
| 3,987,047 | 10/1976 | Griss et al. | 540/580 |
| 4,108,998 | 8/1978 | Demerson et al. | 514/291 |
| 4,631,286 | 12/1986 | Shutske et al. | 514/297 |
| 4,695,573 | 9/1987 | Shutske et al. | 514/290 |
| 4,816,456 | 3/1989 | Summers | 514/255 |
| 4,851,536 | 7/1989 | Skotnicki et al. | 546/106 |
| 4,897,400 | 1/1990 | Shutske | 514/289 |
| 4,985,430 | 1/1991 | Morita et al. | 514/253 |

OTHER PUBLICATIONS

Konshin, et al.,(III), Izv.Vyssh.Ucheb.Zaved.Khim.-Khim.Tekhnol., vol. 15(5), pp. 726–727 (1972) English language version.

Konshin, et al.,(IV),Khim. Geterotsikl.Soedin, English language version 1973(No. 4), pp. 531–534.

Konshin, et al.(V), Khim.-Farm. Zh., English language version vol. 8(7), pp. 17–19 (1974).

Konshin, Nauch.Tr.Prem.Farmstsvet.In-t.vol. 10, pp. 6–9 (1976) English language translation.

Khaldeeva, et al., Khim.Getrotsikl.Soedin. English translation 1976, No. 2,pp. 263–265.

Bialevsky, Collection Czech. Chem. Commun., vol. 42, pp. 2802–2808 (1977).

Krishna, et al., Ind. J. Chem., vol. 16B(2), pp. 156–158 (1978).

Buu-Hoi, et al., Chemical Abstracts, vol. 69:106408d(1968).

Patnaik, et al, J. Med. Chem. 9, pp. 483–488 (1966).

9-AMINO-1,4ETHANO-1,2,3,4-TETRAHYDROACRIDINE AND RELATED COMPOUNDS

This is a continuation-in-part of the prior application Ser. No. 014,753, filed Feb. 13, 1987, now U.S. Pat. No. 4,897,400.

This invention relates to compounds having the formula

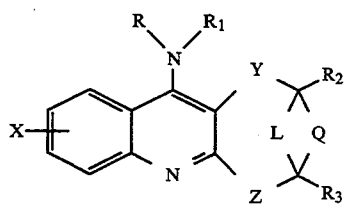

wherein R is hydrogen, loweralkyl or loweralkylcarbonyl; $R_1$ hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; $R_2$ and $R_3$ are independently H or $CH_3$; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —$NHCOR_4$ or —$NR_5R_6$ where $R_4$ is hydrogen or loweralkyl, and $R_5$ and $R_6$ are independently hydrogen, loweralkyl or cycloalkyl; Y and Z are independently a direct bond, $CR_7R_8$ or $CR_7R_8$—$CR_9R_{10}$; and P and Q are independently $CR'_7R'_8$, $CR'_7R'_8$—$CR'_9R'_{10}$, $CR'_7$=$CR'_9$ or $CR'_7R'_8$—$CR'_9R'_{10}$—$CR_{11}R_{12}$, where each of $R_7$ through $R_{12}$ and $R'_7$ through $R'_{10}$ is independently H or $CH_3$; a stereo, optical and geometrical isomers thereof, which are useful for enhancing memos, methods for synthesizing them, and pharmaceutical compositions comprising an effective memory enhancing amount of such a compound, and a method of increasing the cholinergic function in mammals which comprises the administration of an effective amount of such a compound.

This invention also relates to compounds having the formulas

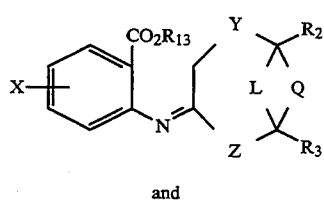

and

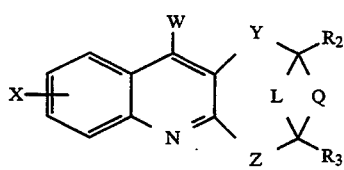

wherein $R_2$, $R_3$, X, Y, Z, L, and Q are as defined above, $R_{13}$ is hydrogen or loweralkyl, and W is halogen, hydroxy or loweralkoxy, which are useful as intermediates for synthesizing the compounds of Formula I.

Throughout the specification and appended claims, a given chemical formula or name shall encompass all stereo, optical and geometrical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes a saturated alicyclic group containing 3 to 7 carbon atoms. Examples of said cycloalkyl include cyclopropyl, cyclohexyl and cycloheptyl.

Unless otherwise stated or indicated, the term loweralkoxy denotes a straight or branched alkoxy group having 1 to 6 carbon atoms. Examples of said loweralkoxy include methoxy, ethoxy, iso-propoxy, sec-butoxy and straight and branched chain hexyloxy.

Unless otherwise stated or indicated, the term halogen shall mean fluorine, chlorine, bromine or iodine.

Unless otherwise stated or-indicated, the term aryl shall mean an unsubstituted phenyl group or a phenyl group substituted with 1, 2 or 3 substituents each of which being independently loweralkyl, loweralkoxy, halogen, hydroxy, trifluoromethyl, phenoxy or benzyloxy.

Unless otherwise stated or indicted, the term oxygen-bridged shall signify the fact that an oxygen atom is present between aryl and loweralkyl groups and/or an oxygen atom has replaced a methylene group in the loweralkyl group, with the proviso that said methylene group is not alpha to the amino nitrogen carrying the groups R and $R_1$. Thus, examples of oxygen-bridged arylloweralkyl include 3-phenoxypropyl and 4-phenoxybutyl, and examples of oxygen-bridged diarylloweralkyl include 2-[bis(4-fluorophenyl)methoxy] ethyl and 2-[bis(3-fluorophenyl) methoxy] ethyl.

The compounds of this invention can be prepared by utilizing one or more of the synthetic steps described below. In order to simplify the description of the synthetic schemes, the description will be presented below with specific reference to the situation where $R_2$ and $R_3$ are hydrogen, Y and Z are direct bond, L is $CH_2$ and Q is $CH_2CH_2$, but it will readily be understood that the synthetic schemes can also be applied to the other situations by making obvious modifications where necessary.

Throughout the description of the synthetic steps, the definitions of R, $R_1$, $R_2$, $R_3$, $R_{13}$, X, Y, Z, L, Q and W are as given above unless otherwise stated or indicted.

STEP A

Compounds of Formula IIa can be prepared by reacting a compound of Formula IV with 2-norbornanone. Said reaction can be conducted in a suitable solvent Such as benzene, toluene or xylene at a temperature of about 80°–150° C. in the presence of an acid catalyst such as p-toluene sulfonic acid, benzenesulfonic acid or methanesulfonic acid.

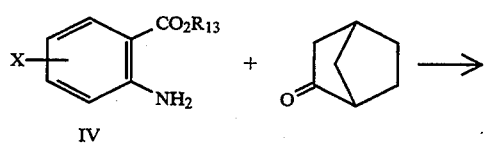

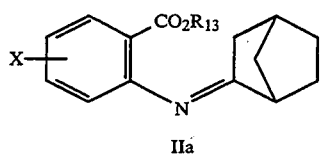

IIa

STEP B

Compounds of Formula IIIa can be prepared by reacting a compound of Formula IIa with phosphorus pentoxide in the presence of a high boiling tertiary amine such as N,N-dimethylcyclohexylamine, Said reaction can be conducted without additional solvent at a temperature of about 170°–220° C.

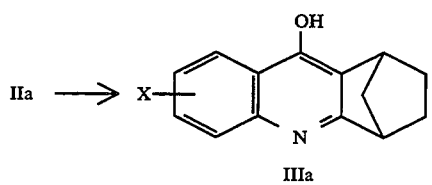

IIIa

The hydroxy group attached to the middle ring of compound IIa can readily be converted to a loweralkoxy group in a routine manner known to the art,

STEP C

Compounds of Formula IIIb can be prepared by reacting a compound of formula IIIa with phosphorus oxychloride and phosphorus pentachloride, Said reaction can be conducted at a temperature of about 100°–150° C.

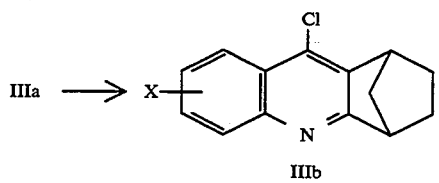

IIIb

The bromine analogue of compound IIIb can be prepared in a similar manner, namely, for instance by reacting compound IIIa with phosphorus oxybromide and phosphorus pentabromide. The fluorine and iodine analogues of compound IIIa can be prepared by replacing the chlorine atom of compound IIIa with fluorine or iodine in a routine manner known to the art.

STEP D

Compounds of Formula VI can be prepared by reacting a compound of formula IIIb with an amine of formula V. Said reaction can be conducted at a temperature of 120°–220° C. in the presence of an acidic catalyst such as ammonium chloride or phenol.

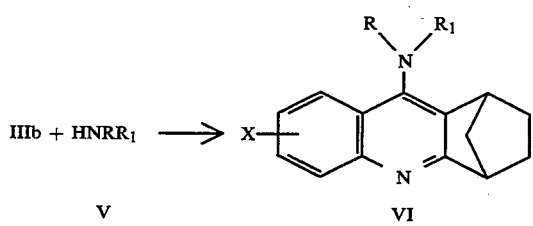

Steps A through D can be combined into a single step. Thus compounds of Formula VI can be obtained by heating together a mixture of phosphorous pentoxide, N,N-dimethylcyclohexylamine and the hydrochloride of amine V and then adding a compound of Formula IV, followed by 2-norbornanone. Said reaction can be carried out at a temperature of about 150°–250° C.

As an alternative to the reaction scheme described above, one can also use the following reaction scheme.

STEP E

Anthranilonitrile (ortho-isomer) is allowed to react with norcamphor to obtain 9-amino- 1,4-methano-1,2,3,4-tetrahydroacridine (Formula VIa).

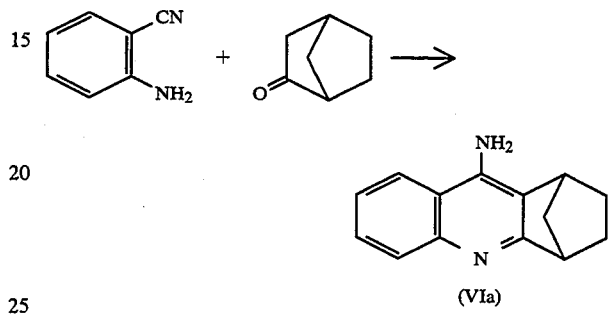

(VIa)

The above reaction is typically conducted in the presence of a suitable catalyst such as freshly fused zinc chloride and a suitable solvent such as nitrobenzene or 1,2-dichloroethane at a temperature of about 80° to 150° C.

Where a cyclic ketone having one or two carbon-carbon double bonds is used in the place of norcamphor in the above reaction, a compound corresponding to compound VIa but having one or two carbon-carbon double bonds in the bicyclic ring moiety is obtained. Thus, for instance, when bicyclo[2,2,2]oct-2-en-5-one is allowed to react with anthranilonitrile (ortho-isomer) in substantially the same manner as described above, 9-amino-1,4-dihydro-1,4-ethanoacridine (Formula VII) is obtained.

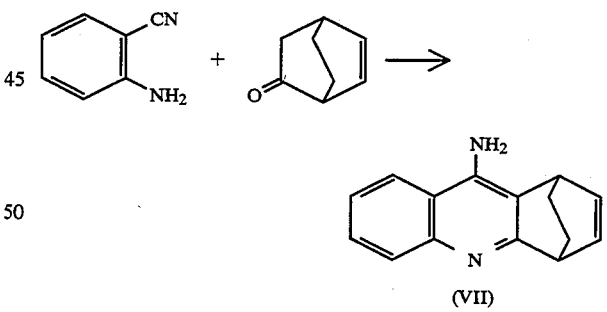

(VII)

STEP F

Compound VIa or VII is reacted with an aldehyde of the formula $R_{14}CHO$ where $R_{14}$ is aryl to afford an imine compound of formula VII or IX, respectively,

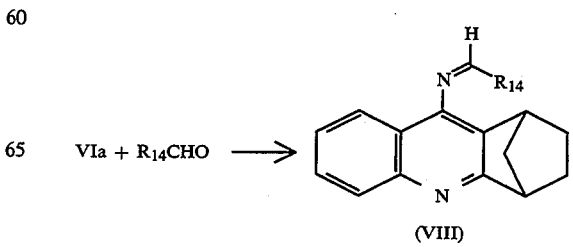

(VIII)

-continued

VII + R₁₄CHO ⟶ 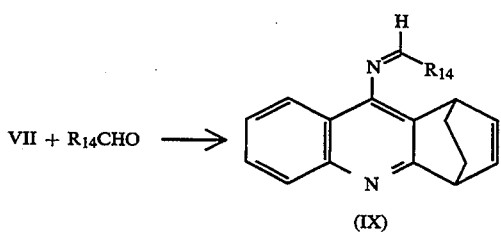
(IX)

The above reactions are typically conducted in a suitable solvent such as benzene, toluene or xylene at a temperature of about 80°–150° C. in the presence of a base such as piperidine, morpholine, diethylamine or diisopropylamine.

STEP G

Compound VIII or IX is reduced with NaBH₃CN to afford a compound of formula X or XI, respectively.

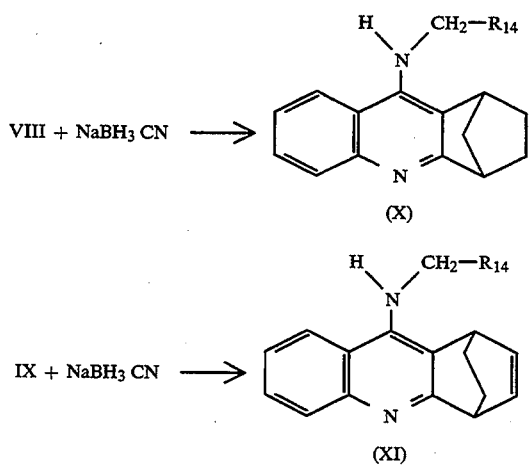

VIII + NaBH₃CN ⟶ (X)

IX + NaBH₃CN ⟶ (XI)

The above reactions are conducted typically in the presence of a suitable medium such as glacial acetic acid at a temperature of 10° to 60° C.

STEP H

Compound XI is catalytically hydrogenated to afford a compound of Formula XII. Palladium catalyst is preferred.

XI + H₂ —Pd→ 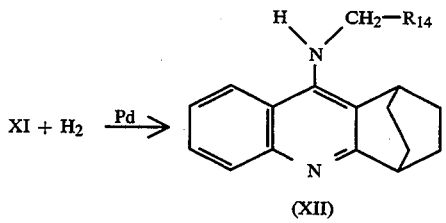
(XII)

The above reaction is typically conducted in the presence of a suitable medium such as absolute ethanol and palladium on carbon at a temperature of about 20° to 50° C.

The compounds of Formula I of the present invention can be used for the treatment of various memory dysfunctions characterized by decreased cholinergic function, such as Alzheimer's disease.

This utility is manifested by the ability of these compounds to inhibit the enzyme acetylcholinesterase and thereby increase acetylcholine levels in the brain.

The ability to inhibit acetylcholinesterase was determined by the photometric method of Ellman et al., Biochem. Pharmacol. 7,88 (1961). Results of acetylcholinesterase inhibition for some of the compounds of this invention are presented in Table 1 along with those for reference compounds.

TABLE 1

Acetylcholinesterase Inhibition Assay

| Compound | Acetylcholinesterase Inhibition IC$_{50}$ (molar) |
|---|---|
| 9-Amino-1,4-methano-1,2,3,4-tetrahydroacridine | $9.3 \times 10^{-8}$ |
| 9-Amino-1,4-methano-6-methyl-1,2,3,4-tetrahydroacridine | $3.0 \times 10^{-7}$ |
| 9-Amino-6-fluoro-1,4-methano-1,2,3,4-tetrahydroacridine | $8.0 \times 10^{-8}$ |
| 9-Amino-1,4-methano-1,2,3,4-tetrahydro-6-trifluoromethylacridine | $4.0 \times 10^{-6}$ |
| 9-Phenylamino-1,4-methano-1,2,3,4-tetrahydroacridine | $>1.0 \times 10^{-3}$ |
| 9-Benzylamino-1,4-methano-1,2,3,4-tetrahydroacridine | $>1.0 \times 10^{-3}$ |
| 9-Benzylamino-1,4-methano-6-methyl-1,2,3,4-tetrahydroacridine | $3.1 \times 10^{-5}$ |
| 9-Benzylamino-1,4-methano-1,2,3,4-tetrahydro-6-trifluoromethylacridine | $>1.0 \times 10^{-3}$ |
| 9-Amino-1,4-dihydro-1,4-ethanoacridine | $1.4 \times 10^{-6}$ |
| 9-Benzylamino-1,4-dihydro-1,4-ethanoacridine | $5.2 \times 10^{-5}$ |
| 9-Amino-1,4-ethano-1,2,3,4-tetrahydroacridine | $6.6 \times 10^{-6}$ |
| 9-Benzylamino-1,4-ethano-1,2,3,4-tetrahydroacridine | $7.8 \times 10^{-5}$ |
| (Reference Compounds) | |
| Tacrine (9-amino-1,2,3,4-tetrahydroacridine) | $3.1 \times 10^{-7}$ |
| Physostigmine | $6.0 \times 10^{-9}$ |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incadescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The test results are expressed as the percent of a group of animals in which the effect of scopolamine is blocked, as manifested by an increased interval between being placed in the test chamber and re-entering the dark compartment. Results of Dark Avoidance Assay for some of the compounds of this invention are presented in Table 2 along with a result for a reference compound.

TABLE 2

Dark Avoidance Assay

| Compound | Dose (mg/kg of body weight, s.c) | % of Animals with Scopolamine Induced Memory Deficit Reversal |
| --- | --- | --- |
| 9-Amino-1,4-methano-1,2,3,4-tetrahydroacridine | 2.5 | 40% |
| 9-Amino-1,4-methano-6-methyl-1,2,3,4-tetrahydroacridine | 2.5 | 36% |
| 9-Amino-6-fluoro-1,4-methano-1,2,3,4-tetrahydroacridine | 0.63 | 9% |
| 9-Amino-1,4-methano-1,2,3,4-tetrahydro-6-trifluoromethylacridine | 0.16 | 20% |
| 9-Phenylamino-1,4-methano-1,2,3,4-tetrahydroacridine (Reference Compound) | 0.16 | 20% |
| Physostigmine | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids-useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound. The solutions or suspensions may also include the following components: a sterile diluent such as water for injection, saline solution, fixed oils, polyethylene glycols, glycerine, propylene glyco or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
9-Amino-1,4-methano-1,2,3,4-tetrahydroacridine
9-Amino-1,4-methano-6-methyl-1,2,3,4-tetrahydroacridine
9-Amino-6-fluoro-1,4-methano-1,2,3,4-tetrahydroacridine
9-Amino-1,4-methano-1,2,3,4-tetrahydro-6-trifluoromethylacridine
9-Phenylamino-1,4-methano-1,2,3,4-tetrahydroacridine
9-Benzylamino-1,4-methano-1,2,3,4-tetrahydroacridine
9-Benzylamino-1,4-methano-6-methyl-1,2,3,4-tetrahydroacridine
9-Benzylamino-1,4-methano-1,2,3,4-tetrahydro-6-trifluoromethylacridine
9-Amino-1,4-dihydro-1,4-ethanoacridine
9-Benzylamino-1,4-dihydro-1,4-ethanoacridine
9-Amino-1,4-ethano-1,2,3,4-tetrahydroacridine
9-Benzylamino-1,4-ethano-1,2,3,4-tetrahydroacridine
9-amino-6-chloro-1,4-methano-1,2,3,4-tetrahydroacridine;
9-amino-1,4-methano-6-methoxy-1,2,3,4-tetrahydroacridine;
9-amino-1,4-methano-7-methyl-1,2,3,4-tetrahydroacridine;
1,4-methano-9-methylamino-1,2,3,4-tetrahydroacridine;
7-chloro-1,4-methano-9-methylamino-1,2,3,4-tetrahydroacridine;
1,4-methano-7-methyl-9-methylamino-1,2,3,4-tetrahydroacridine;
9-benzylamino-7-chloro-1,4-methano-1,2,3,4-tetrahydroacridine;
9-benzylamino-1,4-methano-6-methoxy-1,2,3,4-tetrahydroacridine;

9-phenylamino-6-chloro-1,4-methano-1,2,3,4-tetrahydroacridine;
9-phenylamino-1,4-methano-7-methyl-1,2,3,4-tetrahydroacridine;
9-amino-6-chloro-1,4-ethano-1,2,3,4-tetrahydroacridine;
9-amino-1,4-ethano-6-methoxy-1,2,3,4-tetrahydroacridine;
9-amino-1,4-ethano-7-methyl-1,2,3,4-tetrahydroacridine;
1,4-ethano-9-methylamino-1,2,3,4-tetrahydroacridine;
7-chloro-1,4-ethano-9-methylamino-1,2,3,4-tetrahydroacridine;
1,4-ethano-7-methyl-9-methylamino-1,2,3,4-tetrahydroacridine;
9-benzylamino-7-chloro-1,4-ethano-1,2,3,4-tetrahydroacridine;
0-benzylamino-1,4-ethano-6-methoxy-1,2,3,4-tetrahydroacridine;
9-phenylamino-1,4-ethano-1,2,3,4-tetrahydroacridine
9-phenylamino-6-chloro-1,4-ethano-1,2,3,4-tetrahydroacridine;
9-phenylamino-1,4-ethano-7-methyl-1,2,3,4-tetrahydroacridine;
1-amino-6,9-methano-7,8,9,10-tetrahydro-6H-cyclohepta[b]quinoline;
3-chloro-6,9-methano-11-methylamino-7,8,9,10-tetrahydro-6H-cyclohepta[b]quinoline;
11-benzylamino-6,9-methano-2-methyl-7,8,9,10-tetrahydro-6H-cyclohepta[b]quinoline;
11-phenylamino-6,9-methano-3-methoxy-7,8,9,t0-tetrahydro-6H-cyclohepta[b]quinoline.

The following examples are presented in order to illustrate this invention.

EXAMPLE 1

9-Amino-1,4-methano-1,2,3,4-tetrahydroacridine

Anthranilonitrile (2.40 g) was mixed together with norcamphor (4.40 g) and then 4.0 g of freshly fused $ZnCl_2$ was added and the reaction mixture was heated at 120° C. After 1.5 hours it became so thick that it could nod be stirred, so 10 ml of 1,2-dichloroethane was added and the reaction mixture was refluxed for 1 hour. At the end of this time, 40 ml of 10% NaOH was added and the mixture was stirred overnight. It was then extracted several times with 2-butanone which gave a crude product that was purified by flash chromatography (EtOAc, then 5% $Et_2NH$-EtOAc) to give 3.036 g of a foam. Recrystallization from $CH_2Cl_2$-pentane gave 2.303 g of analytically pure product, m.p. 186°–188°.
ANALYSIS:
Calculated for $C_{14}H_{14}N_2$: 79.96% C 6.71% H 13.33% N
Found: 79.85% C 6.65% H 13.13% N

EXAMPLE 2

9-Amino-1,4-methano-6-methyl-1,2,3,4-tetrahydroacridine

A solution of 2-amino-4-methylbenzonitrile (16.0 g) and zinc chloride (24.7 g) in 70 ml of nitrobenzene was heated at 50° C. for 1 hour. To this was added norcamphor (20.0 g) and the mixture was stirred at 130° C. for 3 hours. The reaction mixture was cooled and diluted with ether and the zinc complex was filtered. This complex was partitioned between aqueous $NH_4OH$ and 2-butanone (MEK) and the aqueous phase was extracted with MEK. The organics were washed with water, dried (saturated NaCl, $MgSO_4$) and concentrated to an oil which was triturated with ether to give 12.8 g of a white powder, m.p. 159°–162° C. A 4.0 g portion was recrystallized from isopropyl ether to give 2.5 g of an analytically pure white solid, m.p. 162°–164° C.
ANALYSIS:
Calculated for $C_{15}H_{16}N_2$: 80.32% C 7.19% H 12.49% N
Found: 80.29% C 7.05% H 12.52% N

EXAMPLE 3

9-Amino-6-fluoro-1,4-methano-1,2,3,4-tetrahydroacridine

To a solution of 2-amino-4-fluorobenzonitrile (4.59 g) in 20 ml of nitrobenzene was added freshly fused, pulverized ZnCl2 (6.9 g)., This was heated at 50° C. for 1 hour and thereafter 5.6 g of norcamphor was added. This was stirred at 130° C. for 1.5 hours and the resulting precipitate was filtered, rinsed with ethyl ether and partitioned between 2-butanone and aqueous $NH_4OH$ solution. The organic phase was washed with water and dried ($MgSO_4$). Evaporation of the solvent gave a solid which was triturated with ether/hexane to give 3.95 g of a tan powder. This was recrystallized from ether/hexane to give 2.28 g of a white solid, m.p. 194°–195° C.
ANALYSIS:
Calculated for $C_{14}H_{13}FN_2$: 73.66% C 5.74% H 12.27% N
Found: 73.44% C 5.76% H 12.15% N

EXAMPLE 4

9-Amino-1,4-methano-1,2,3,4-tetrahydro-6-trifluoromethylacridine

To a solution of 2-amino-4-trifluoromethylbenzonitrile (12.8 g) in 50 ml of nitrobenzene was added freshly fused and pulverized $ZnCl_2$ (14.1 g). This was heated at 50° C. fo 1 hour and to this mixture was added norcamphor (11.4 g). The reaction mixture was heated at 130° C. for 3 hours, after which it was cooled, diluted with ethyl ether and filtered. The resulting solid was partitioned between 2-butanone (MEK) and aqueous $NH_4OH$ and the aqueous portion was extracted with MEK. The combined organics were washed with water, dried (satureatd NaCl, $MgSO_4$) and concentrated to a solid which was triturated with ether/hexane to give 10.3 g of a white powder, m.p. 174°–179° C. A 4.0 g portion was recrystallized from methanol/water to give 3.5 g of an analytically pure white powder, m.p. 175°–178° C.
ANALYSIS:
Calculated for $C_{15}H_{13}F_3N_2$: 64.74% C 4.71% H 10.07% N
Found: 64.70% C 4.88% H 10.09% N

EXAMPLE 5

9-Phenylamino-1,4-methano-1,2,3,4-tetrahydroacridine

Phosphorus pentoxide (28.4 g), N,N-dimethylcyclohexylamine (25.4 g) and aniline hydrochloride (25.9 g) were mixed well at from temperature and then heated on an oil bath at 220° until a homogenous mixture was obtained (ca. 45 min). The mixture was then allowed to cool to 130° and methyl anthranilate (7.58 g) was added dropwise, followed by norcamphor (6.61 g). The mixture was heated again at 220° for a total of 20 hours, at which time it was allowed to cool to 100°. Aqueous sodium hydroxide solution (450 ml of 2M) was then added and stirring was continued at 100° for 30 minutes. The product was isolated by extracting the cooled reaction mixture with EtOAc, concentrating under reduced pressure and then triturating the residue with Et$_2$O. In this manner, 6.28 g of product was obtained, m.p. 223°–225°

ANALYSIS:

Calculated for C$_{18}$H$_{20}$N$_2$: 9.78% N 8:3.88% C 6.33% H

Found: 83.67% C 6.32% H 9.99% N

EXAMPLE 6

9-Benzylamino-1,4-methano-1,2,3,4-tetrahydroacridine 1,4-Methano-1,2,3,4-tetrahydro-9-acridinamine (8.40 g) was refluxed in 300 ml of toluene that contained 7.0 g of morpholine and 6.4 g of benzaldehyde that had been freshly washed with aqueous K$_2$CO$_3$. The reaction mixture was refluxed overnight and then concentrated and purified by flash chromatography (20% EtOAc-CH$_2$Cl$_2$) to give 9.51 g of chromatographically pure product. Analytically pure material was obtained by recrystallization from benzene/pentane, m.p. 128°–130°.

1,4-Methano-N-(phenylmethylene)-1,2,3,4-tetrahydro-9-acridinamine (4.0 g) obtained above was dissolved in 40 ml of HOAc and treated with 1.0 g of NaCNBH$_3$. After 30 minutes, the solvent was removed under reduced pressure and the residue was distributed between 10% NaOH and CH$_2$Cl$_2$. Concentration of the organic phase and recrystallization from MeOH gave 2.35 g of analytically pure product, m.p. 205°–206°.

ANALYSIS:

Calculated for C$_{21}$H$_{20}$N$_2$: 83.96% C 6.71% H 9.33% N

Found: 84.37% C 6.87% H 9.43% N

EXAMPLE 7

9-Benzylamino-1,4-methano-6-methyl-1,2,3,4-tetrahydroacridine

A solution prepared from 9-amino-1,4-methano-6-methyl-1,2,3,4-tetrahydroacridine (8.86 g), benzaldehyde (6.3 g, freshly washed with K$_2$CO$_3$ solution), morpholine (6.9 ml) and 300 ml of toluene was refluxed, with removal of water, for 18 hours. At this time, another equivalent of benzaldehyde was added and reflux was continued for 24 hours. The solvent was then removed in vacuo and the imine was purified via flash chromatography (dichloromethane) to give 7.3 g of an orangish solid, m.p. 144°–147° C. A 3.5 g :portion was recrystallized from isopropyl ether to give 2.53 g of light yellow crystals, m.p. 149°–152° C.

To a solution of the imine (3.9 g) obtained above in 40 ml of glacial acetic acid was added portionwise sodium cyanoborohydride (1.18 g). This was stirred for 1 hour at ambient temperature and the acetic acid was concentrated off. The resulting semi-solid was stirred with ethyl acetate and 10% NaOH and the resulting solid was filtered, rinsed with water and dried to give 3.7 g of a white powder. This was recrystallized from methanol to give 2.1 g of a white solid, m.p. 220°–224° C.

ANALYSIS:

Calculated for C$_{22}$H$_{22}$N$_2$: 84.04% C 7.05% H 8.91% N

Found: 84.39% C 7.20% H 8.93% N

EXAMPLE 8

9-Benzylamino-1,4-methano-1,2,3,4-tetrahydro-6-trifluoromethylacridine

A mixture prepared from 9-amino-1,4-methano-1,2,3,4-tetrahydro-6-trifluoromethylacridine (7.65 g), benzaldehyde (4.4 g, freshly washed with K$_2$CO$_3$), morpholine (4.8 ml) and 300 ml of toluene was refluxed with removal of water for 18 hours. At this point, an additional 4.4 g of benzaldehyde was added and reflux was continued for 24 hours.

The reaction mixture was then concentrated to a solid and the residue was chromatographed (dichloromethane) to give 8.3 g of an orange solid, m.p. 120°–126° C. A 4.07 g portion was recrystallized from cyclohexane to give 2.56 g of an off-white solid, m.p. 127°–130° C.

To a solution of the imine (4.1 g) obtained above in 45 ml of glacial acetic acid was added sodium cyanoborohydride (1.05 g). This was stirred for 2 hours at ambient temperature and then concentrated to an oil. This was partitioned between 10% NaOH solution and ethyl acetate and the aqueous phase was extracted with ethyl acetate. The combined organics were washed with water and dried (MgSO$_4$). The solvents were removed by evaporation to give 3.6 g of a yellow solid, m.p. 171°–179° C., which was then recrystallized from methanol/water to give 2.92 g of a white solid, m.p. 180°–183° C.

ANALYSIS:

Calculated for C$_{22}$H$_{19}$F$_3$N$_2$: 71.72% C 5.20% H 7.60% N

Found: 71.36% C 5.13% H 7.53% N

EXAMPLE 9

9-Amino-1,4-dihydro-1,4-ethanoacridine

A mixture prepared from anthranilonitrile (4.18 g), freshly fused zinc chloride (7.2 g) and 15 ml of nitrobenzene was heated at 50° C. for 45 minutes. To the resulting suspension was added bicyclo[2.2.2]oct-2-en-5-one (6.5 g) and this was heated at 130° C. for 1.5 hours.

The reaction mixture was cooled and treated with ethyl ether, and the precipitate was filtered, rinsed with ether and then partitioned between 2-butanone (MEK) and aqueous NH$_4$OH solution. The aqueous phase was extracted with MEK and the organics were washed with water and dried (saturated NaCl, MgSO$_4$). Removal of the solvents gave 5.7 g of an off-white powder which was recrystallized from methanol/water to give 4.76 g of an off-white solid, m.p. 218°–220° C. d.

ANALYSIS:

Calculated for C$_{15}$H$_{14}$N$_2$: 81.05% C 6.35% H 12.60% N

Found: 80.296% C 6.34% H 12.65% N

EXAMPLE 10

9-Benzylamino-1,4-dihydro-1,4-ethanoacridine

A mixture prepared form 9-amino-1,4-dihydro-1,4-ethanoacridine (11.4 g), benzaldehyde (8.2 g, freshly washed with K$_2$CO$_3$ solution), morpholine (9.0 ml) and 350 ml of toluene was refluxed with removal of water for 18 hours. An additional 6 g of benzaldehyde was added and the reflux was continued for 12 hours with removal of water.

The reaction mixture was concentrated, passed through a column of florisil (dichloromethane) and the imine was purified via flash chromatography (DCM;

5% EtOAc/DCM) to give 13.4 g of an orangish solid. A 3.0 g portion was recrystallized from methanol/water to give 2.54 g of light yellow crystals, m.p. 178°–180° C.

To a stirred solution of the imine (4.65 g) obtained above in 50 ml of glacial acetic acid was added sodium cyanoborohydride (1.4 g). This was stirred at ambient temperature for 2 hours, the acetic acid was concentrated off and the residue was treated with 10% NaOH and ethyl acetate which after filtration gave 3.2 g of a white solid. This was recrystallized from methanol/water to give 2.60 g of white crystals, m.p. 166°–168° C.
ANALYSIS:

Calculated for $C_{22}H_{20}N_2$: 84.58% C 6.45% H 8.97% N

Found: 84.36% C 6.45% H 8.96% N

EXAMPLE 11

9-Amino-1,4-ethano-1,2,3,4-tetrahydroacridine

A solution of 9-amino-1,4-dihydro-1,4-ethanoacridine (5.30 g) in 125 ml of absolute ethanol was added to a suspension of 10% Pd on charcoal in EtOH, in a Parr pressure flask. This was pressurized to 45 psi with hydrogen gas and shaken for 3 hours.

The catalyst was filtered and the solvent concentrated off to give 5.3 g of a yellowish solid, m.p. 222°–226° C.
ANALYSIS:

Calculated for $C_{15}H_{16}N_2$: 80.32% C 7.19% H 12.49% N

Found: 80.35% C 7.22% H 12.56% N

EXAMPLE 12

9-Benzylamino-1,4-ethano-1,2,3,4-tetrahydroacridine

A mixture of 9-benzylamino-1,4-dihydro-1,4-ethanoacridine (5.17 g) and 10% Pd/C (161 mg) in 200 ml of absolute ethanol was agitated for 30 hours under 41 psi of hydrogen gas.

The catalyst was then filtered and the solvent concentrated in vaccum to give 5.1 g of a greenish solid, m.p. 136°–140° C. This was recrystallized from methanol/water to give 4.46 g of a white powder, m.p. 139°–141° C.
ANALYSIS:

Calculated for $C_{22}H_{22}N_4$: 84.04% C 7.05% H 8.91% N

Found: 84.21% C 7.04% H 8.96% N
We claim:

1. A compound of the formula

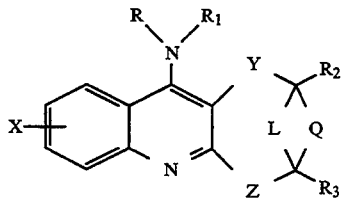

wherein

R is hydrogen or loweralkyl;

$R_1$ is hydrogen, loweralkyl, aryl, diloweralkylaminoloweralkyl, arylloweralkyl, diarylloweralkyl, aryl$(CH_2)_m$—O—$(CH_2)_l$— or diarylCH$(CH_2)_k$—O—$(CH_2)_l$—; wherein aryl is unsubstituted phenyl or phenyl substituted with 1, 2 or 3 substituents each of which being independently loweralkyl, loweralkoxy, halogen, hydroxy, trifluoromethyl, phenoxy or benzyloxy;

m is 0, 1, 2, 3 or 4;

l is 2, 3, 4, or 5;

k is 0, 1, 2, or 3; wherein the sum of m+l is <6 and the sum of k+l is <5;

$R_2$ and $R_3$ are independently H or $CH_3$;

X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_4$ or NR$_5$R$_6$ where R$_4$ is hydrogen or loweralkyl, and R$_5$ and R$_6$ are independently hydrogen, loweralkyl, and cycloalkyl; Y and Z are independently a direct bond, CR$_7$R$_8$ or CR$_7$R$_8$—CR$_9$R$_{10}$; and L and Q are independently CR'$_7$R'$_8$, CR'$_7$R'$_8$,—CR'$_9$R'$_{10}$, CR'$_7$=CR'$_9$ or C—R'$_7$R'$_8$—CR'$_9$R'$_{10}$—CR$_{11}$R$_2$, where each of R$_7$ through R$_{12}$ and R'$_7$ through R'$_{10}$ is indepndently H or CH$_3$; a stereo, optical and geometrical isomer thereof, and a pharmaceutically acceptable acid addition salt thereof.

2. The compound as defined in claim 1, where R is hydrogen and R$_1$ is hydrogen or arylloweralkyl.

3. The compound as defined in claim 1, where X is hydrogen, loweralkyl or trifluoromethyl.

4. The compound as defined in claim 1, which is 9-amino-1,4-methano-6-methyl-1,2,3,4-tetrahydroacridine.

5. The compound as defined in claim 1, which is 9-amino-6-fluoro-1,4-methano-1,2,3,4-tetrahydroacridine.

6. The compound as defined in claim 1, which is 9-amino-1,4-methano-2,3,4-tetrahydro-6-trifluoromethylacridine.

7. The compound as defined in claim 1, which is 9-benzylamino-1,4-methano-6-methyl-1,2,3,4-tetrahydroacridine.

8. The compound as defined in claim 1, which is 9-benzylamino-1,4-methano-2,3,4-tetrahydro-6-trifluoromethylacridine.

9. The compound as defined in claim 1, which is 9-amino-1,4-dihydro-1,4-ethanoacridine.

10. The compound as defined in claim 1, which is 9-benzylamino-1,4-dihydro-1,4-ethanoacridine.

11. A pharmaceutical composition for increasing the cholinergic function in a mammal which comprises an effective amount of a compound as defined in claim 1 and a carrier therefor.

12. A method of increasing the cholinergic function in a mammal which comprises administering to the mammal an effective cholinergic function increasing amount of a compound as defined in claim 1.